United States Patent [19]
Vroblesky et al.

[11] Patent Number: 5,804,743
[45] Date of Patent: Sep. 8, 1998

[54] DOWNHOLE PASSIVE WATER SAMPLER AND METHOD OF SAMPLING

[75] Inventors: Don A. Vroblesky, Columbia; William Thomas Hyde, Jr., Easley, both of S.C.

[73] Assignee: General Electric Company, Schenectady, N.Y.

[21] Appl. No.: 700,047

[22] Filed: Aug. 20, 1996

[51] Int. Cl.$^6$ .................................................. E21B 49/08
[52] U.S. Cl. ................. 73/863.23; 73/64.56; 73/864.51; 166/264
[58] Field of Search ............................ 73/863.23, 864.51, 73/64.56, 19.12; 166/264

[56] References Cited

U.S. PATENT DOCUMENTS

| | | | |
|---|---|---|---|
| 3,367,850 | 2/1968 | Johnson | 73/863.23 X |
| 3,715,913 | 2/1973 | Anderson | 73/864.51 X |
| 3,929,003 | 12/1975 | Llewellyn | 73/61.72 |
| 4,078,433 | 3/1978 | Mc Lobe, Jr. et al. | 73/864.61 |
| 4,516,580 | 5/1985 | Polonyi | 73/863.23 X |
| 4,692,287 | 9/1987 | Timmon | 73/863.23 X |
| 4,763,658 | 8/1988 | Jones | 73/863.23 X |
| 5,110,473 | 5/1992 | Hassett | 210/634 |
| 5,147,561 | 9/1992 | Burge et al. | 73/863.23 X |
| 5,442,968 | 8/1995 | Westlake, III et al. | 73/863.23 |
| 5,454,275 | 10/1995 | Kasis | 73/864.51 |
| 5,589,647 | 12/1996 | Jax et al. | 73/863.22 |

FOREIGN PATENT DOCUMENTS

| | | | |
|---|---|---|---|
| 795533 | 10/1968 | Canada | 73/863.23 |

OTHER PUBLICATIONS

Alena Murdroch, M.Sc. and Scott D. MacKnight, Ph.D., editors, CRD Handbook of Techniques for Aquatic Sediments Sampling, CRC Press, 1991. pp. 179–184, 198.

Don A Vroblesky and Michelle M. Lorah, "Prospecting for Zones of Contaminated Ground–Water Discharge to Streams Using Bottom–Sediment Gas Bubbles", Ground Water, vol. 29, No. 3, May–Jun. 1991., pp. 333–340.

Don A. Vroblesky, Michelle M. Lorah, Stephen P. Trimble, "Mapping Zones of Contaminated Ground–Water Discharge Using Creek–Bottom–Sediment Vapo Samplers, Aberdeen Proving Ground, Maryland", Ground Water, vol. 29, No. 1, Jan.–Feb., 1991. pp. 7–12.

D. A. Vroblesky, J.F. Robertson, Temporal Changes in VOC Discharge to Surface Water From a Fractured Rock Aquifer During Well Installation and Operation, Greenville, South Carolina, Ground Water Monitoring & REmediation, vol. XVI, No. 3, Summer 1996. pp. 196–201.

Don A. Vroblesky, J. Frederick Robertson, Mario Fernandez, C. Majorie Aelion, "The Permeable–Membrane Method of Passive Soil–Gas Collection", Proceedings of the Sixth National Outdoor Action Conference, May 11–13, 1992 Riviera Hotel, Las Vegas, Nevada. pp. 3–16.

*Primary Examiner*—Thomas P. Noland
*Attorney, Agent, or Firm*—James Magee, Jr.; Douglas E. Stoner

[57] ABSTRACT

An improved method and apparatus for monitoring the concentration of contaminants, including volatile organic compounds, in groundwater is provided comprising a semipermeable membrane defining an inner chamber therein. The membrane is permeable to contaminants but impermeable to a reference fluid, which is preferably distilled water. The method of sampling comprises placing the semipermeable membrane, which contains the reference fluid, in contact with contaminated groundwater, thereby allowing contaminants to diffuse through the semipermeable membrane and into the inner chamber. Sufficient time is allowed for the contaminant concentrations in the groundwater and in the reference fluid to reach equilibrium. The semipermeable membrane is then removed from contact with the groundwater, and a sample withdrawn from the inner chamber for analysis, preferably through a port communicating with the inner chamber.

20 Claims, 3 Drawing Sheets

DOWNHOLE PASSIVE WATER SAMPLER AND METHOD OF SAMPLING

BACKGROUND OF THE INVENTION

This invention relates generally to a liquid sampling device, and more particularly to an improved method and apparatus for monitoring the concentration of contaminants, including volatile organic compounds, in groundwater.

Various devices exist for sampling a liquid. DMLS™ is a passive, multi-layer sampling device which is used to extract groundwater samples. DMLS™ is comprised of a rod (or connector rods) with apertures at specific intervals to accommodate dialysis cells. Contaminants enter the dialysis cells by diffusion.

U.S. Pat. No. 5,454,275 to Kabis discloses a groundwater sampler which makes use of pressure differentials that result during sampling. U.S. Pat. No. 5,147,561 to Burge et al. teaches a sampling device containing a stripping chamber for stripping a groundwater sample of its volatile components at or near the point of collection. U.S. Pat. No. 4,078,433 to McCabe, Jr. et al. discloses a liquid sampling device comprising a length of pipe having a cap screwed onto each end thereof. The upper cap has an aperture for admitting the liquid to be sampled into the pipe.

Despite the prior art devices, there is much room for improvement in the art of groundwater sampling.

SUMMARY OF THE INVENTION

It is therefore an object of this invention to provide an improved method and apparatus for sampling groundwater.

It is another object of this invention to provide an improved method and apparatus for sampling groundwater that does not require the purging of a well.

It is another object of this invention to provide an improved method and apparatus for sampling groundwater that can be used subaqueously.

It is yet another object of this invention to provide an improved method and apparatus for sampling groundwater that precludes the need for an organic-carbon sorbent.

It is yet another object of this invention to provide an improved method and apparatus for sampling groundwater that precludes the need for dialysis cells.

It is still another object of this invention to provide an improved method and apparatus for sampling groundwater that utilizes water as a carrier for volatile organic compounds and other contaminants.

It is still another object of this invention to provide an improved method and apparatus for sampling groundwater that is both economical and environmentally friendly.

It is still a further object of this invention to provide an improved method and apparatus for sampling groundwater that is easy to construct and use.

These and other objects of the invention are achieved by a passive water sampler comprising: a semipermeable membrane, the semipermeable membrane being permeable to contaminants and impermeable to a reference fluid; the semipermeable membrane defining an inner chamber herein; and the inner chamber being at least partially filled with the reference fluid, the partially filled semipermeable membrane being placed in contact with the groundwater thereby allowing the contaminants to diffuse through the semipermeable membrane and into the inner chamber, the concentrations of the contaminants in the groundwater and in the reference fluid coming into equilibrium.

DETAILED DESCRIPTION

Figure 1:
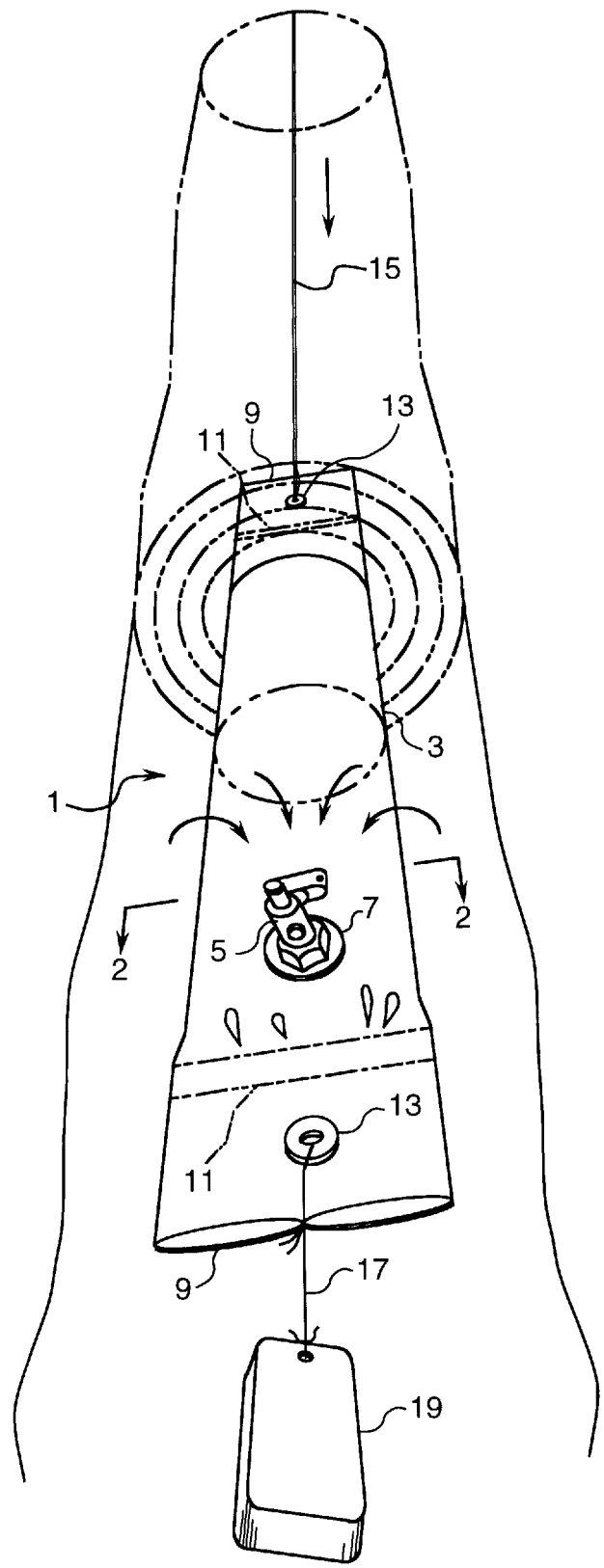
FIG. 1 is a front elevational view of a preferred embodiment of the present invention.

The method and apparatus according to this invention can be used to monitor the concentrations of volatile organic compounds (VOCs) and other contaminants in groundwater without the need to purge a well. Purging a well is presently a regulatory requirement if samples are to be withdrawn from the well, and is a large part of the expense associated with routine monitoring of groundwater contamination. Regulatory agencies typically require removal of at least three casing volumes of water prior to sampling. The large number of observation wells typically sampled at groundwater contamination sites results in a large volume of contaminated purge water that must be disposed of. Thus, sampling costs are incurred that include not only personnel time, but also the proper transport and disposal of the contaminated purge water. These costs can be substantial when multiplied over the lifetime of the contamination. Moreover, the costs associated with remediation and monitoring of existing groundwater contamination must be factored in as a loss when the market value of particular businesses are calculated. The method and apparatus of sampling according to the present invention eliminates the need to purge wells, thus resulting in a substantial cost savings as well as an increased corporate value. Also, the absence of purging makes the present invention environmentally friendly.

Furthermore, the method and apparatus according to the present invention precludes the need for using either dialysis cells or an organic-carbon sorbent. Both of these can be very costly in terms of sampler preparation and analysis. Also, when using a carbon sorbent, the results obtained yield only relative concentrations because the sorbent continues to collect contaminants, including VOCs, as long as the sampler is in the sampling area. Thus, using the sorbent system, the measured contaminant concentration is a function of the time the simpler was in place. On the other hand, the present invention allows the contaminant concentration in the sampler to change in response to fluctuations in contaminant concentrations outside of the sampler, thereby maintaining equilibrium and providing an accurate contaminant concentration in the sampler at any time after equilibrium is reached. Consequently, great flexibility is allowed in the length of time that the present invention can be left in the sampling area.

Additionally, the present invention is used subaqueously, thus accomplishing its objectives without requiring the pumping or bailing of water samples from within a well. It has been found that water immediately adjacent to a well screen can be representative of an aquifer without having to purge, and may even be more favorable than samples achieved after purging due to the sampling bias that can result from the purging itself.

Therefore, according to this invention, it has been found that an improved method and apparatus for water sampling can be utilized. This and other features of the invention will become apparent from the description that follows with particular reference to the figures of drawing.

Referring to the drawings, FIG. 1 shows a front elevational view of the preferred embodiment of the downhole passive water sampler 1 according to the present invention. Downhole passive water sampler 1 comprises at least semipermeable membrane 3. Semipermeable membrane 3 is constructed to be permeable to contaminants, including VOCs, but impermeable to a reference fluid. The reference fluid employed is preferably distilled water, but may be undistilled water or any other suitable fluid. The use of water simplifies the analytical aspects of the system. Semipermeable membrane 3 can be made from a variety of materials which fit the above-stated criteria, but is preferably made from polyethylene. It is envisioned that other polymers, such as polypropylene, may also be employed. Semipermeable membrane 3 may be manufactured in a wide variety of shapes and sizes depending on the application. Water sampler 1 is relatively small, making it easily transportable.

Figure 2:
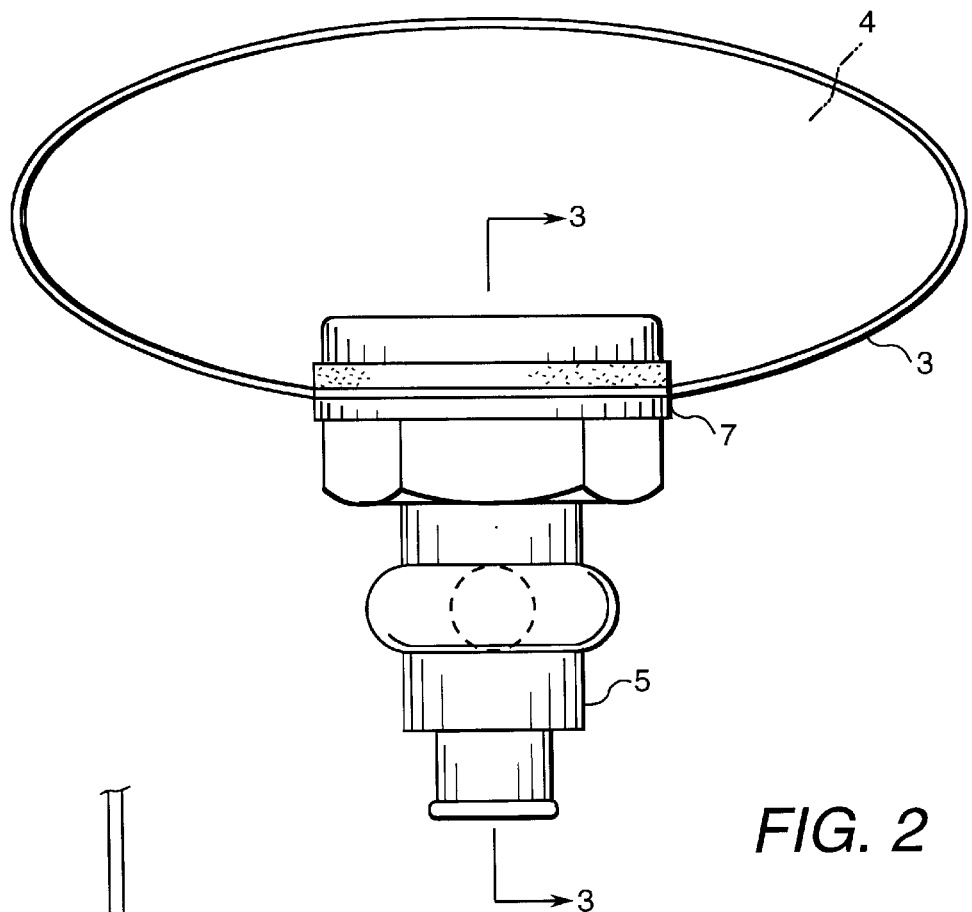
FIG. 2 is a cross-sectional plan view of a preferred embodiment of the present invention taken along line 2—2 of FIG. 1.

Semipermeable membrane 3 defines inner chamber 4 therein (FIG. 2). Preferably, semipermeable membrane 3 is provided in the shape of a tube having open ends. In this case, inner chamber 4 is formed by sealing the open ends of the tubes, thus providing a leakage-free inner chamber 4. This sealing may be achieved by: heat sealing, sonic welding, or any other suitable bonding method. FIG. 1 shows the resulting top and bottom seals 11.

Figure 4:
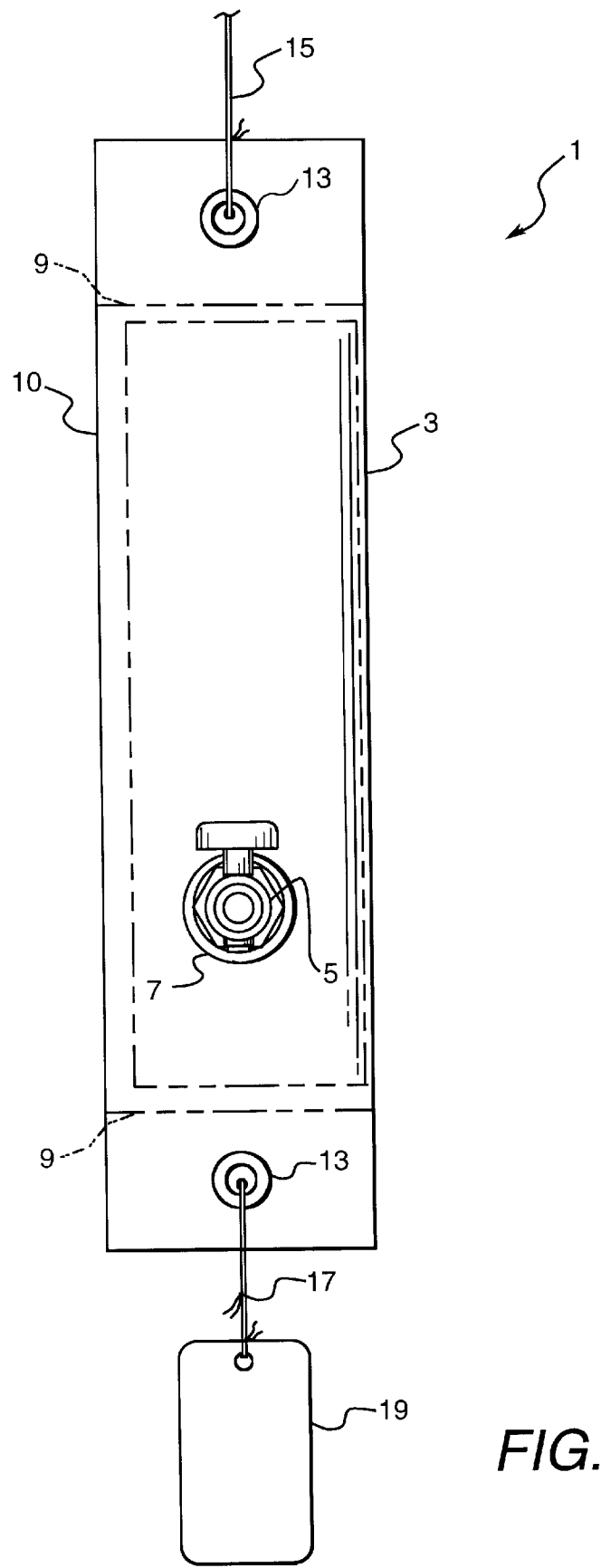
FIG. 4 is a front elevational view of an alternative embodiment of the present invention.

Alternatively, semipermeable membrane 3 may be provided as a flat piece. In this case, inner chamber 4 is formed by folding semipermeable membrane 3 over and onto itself, thereby forming one folded edge and three overlapping edges. Next, the three overlapping edges are respectively sealed together, forming top and bottom seals 9 and a side seal 10 (as shown in FIG. 4).

Figure 3:
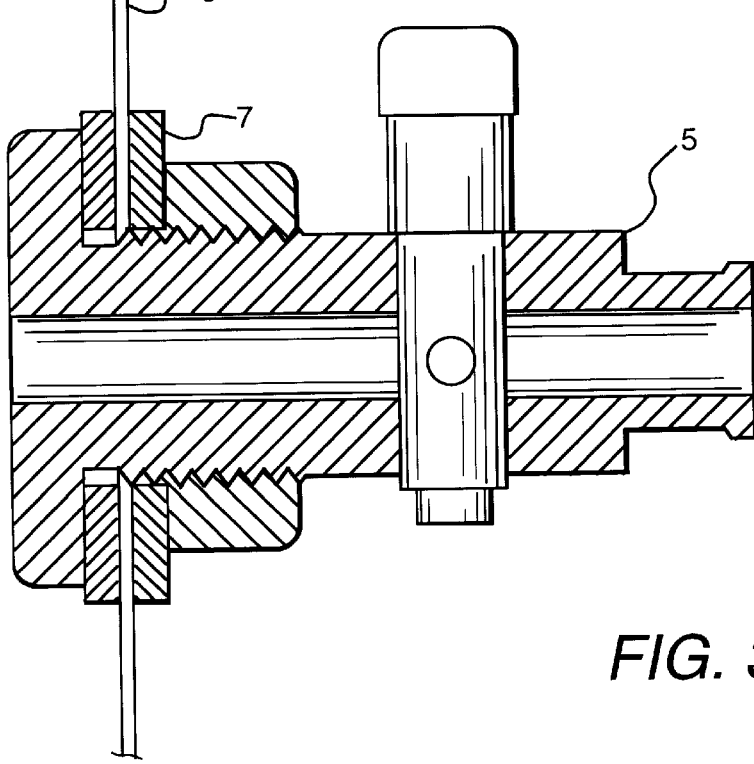
FIG. 3 is a side view of a port suitable for use in a preferred embodiment of the present invention.

Prior to placing water sampler 1 in contact with contaminated groundwater, inner chamber 4 is at least partially filled with the reference fluid. Preferably, the reference fluid is added to inner chamber 4 through port 5 which communicates with both inner chamber 4 and an area outside of semipermeable membrane 3 (FIG. 3) through hole 6. Other appropriate means for adding or withdrawing fluid that communicates with both inner chamber 4 and an area outside of semipermeable membrane 3 may also be employed. Port 5 is preferably made from TEFLON™, but the material of construction may vary depending on the application. Port 5 can also employ a locking nut. Port 5 is preferably connected to semipermeable membrane 3 by washer 7 in a manner that prevents leakage of the reference fluid from inner chamber 4. Washer 7 is preferably a Viton Washer, but the material of construction may vary depending on the application. Hole 6 can be opened or closed by the turning of handle 8.

Upon placing partially filled semipermeable membrane 3 in contact with contaminated groundwater, the contaminants in the groundwater come into contact with semipermeable membrane 3. The contaminants begin to diffuse through semipermeable membrane 3 and into inner chamber 4. As discussed above, semipermeable membrane 3 is impermeable to the reference fluid contained therein, and thus the reference fluid does not diffuse into the groundwater. Likewise, semipermeable membrane 3 is impermeable to the groundwater itself, and thus only contaminants in the groundwater diffuse into inner chamber 4. Contaminants continue to diffuse into inner chamber 4 until the concentration of contaminants in the reference fluid and the concentration of contaminants in the groundwater reach equilibrium. As discussed above, water sampler 1 may be submerged in a well for great lengths of time without jeopardizing analysis results. This is because, once equilibrium has been reached, any changes in contaminant concentration outside of water sampler 1 are compensated for diffusion of contaminants into or out of inner chamber 4. Thus, equilibrium is consistently maintained. For example, if the concentration of contaminants in the groundwater falls, contaminants, will diffuse out of inner chamber 4 and into the groundwater until the contaminant concentrations in the reference fluid and in the groundwater are the same again. Conversely, if the contaminant concentration in the groundwater rises, contaminants, will diffuse from the groundwater into inner chamber 4 until the concentrations are the same again.

When water sampler 1 is to be used in a well, as is preferred, it is preferred to attach plastic members 9 to opposite sides of semipermeable membrane 3. Plastic members 9 have grommets 13 therein, grommets 13 being made of plastic, metal, or other suitable material depending on the application. Attached to one of grommets 13 is support line 15. Support lines 15 is of suitable length and construction for supporting water sampler 1 while inside a well. Support line 15 may be tied to an above ground portion of the well during sampling. Support line 15 is used to raise water sampler 1 up and out of the well after sampling.

Weight 19 can be hung from the other of grommets 13 either directly or by support line 17 (as shown in FIG. 1). Weight 19 is used to assist in submerging water sampler 1 once it is inside of a well. Weight 19 may be made of a variety of materials and sizes depending on the application. Support lines 15 and 17 may be made from a variety of materials including galvanized steel cable, stainless steel cable, or monofilament line.

Alternatively, a weighted support line can be attached to at least one of grommets 13 for raising and lowering water sampler 1 and to assist in the submerging of water sampler 1.

The method of sampling according to the present invention involves using water sampler 1 in any of its many variations as described above. In the preferred embodiment, inner chamber 4 is first at least partially filled with a reference fluid, preferably distilled water. The reference fluid is preferably added to inner chamber 4 through port 5 communicating therewith. Next, semipermeable membrane 3 is lowered into a well using support line 15. As discussed above, means for submerging water sampler 1 within the groundwater in a well can also be provided.

When the contaminants in the groundwater begin to contact semipermeable membrane 3, they diffuse through semipermeable membrane 3 and into inner chamber 4. After sufficient time, the concentrations of contaminants in the reference fluid and in the groundwater reach equilibrium, as described above.

Once sampling is complete (i.e., once equilibrium has been reached), water sampler 1 is raised up and out of a well using support line 15. A portion of the equilibrium mixture of reference fluid and contaminants within inner chamber 4 can be withdrawn, preferably through port 5, for analysis. Analysis of the sample is carried out by conventional means, for example, through the use of a gas chromatograph. Because the water adjacent to a well screen in an unpurged well is potentially representative of the water in the adjacent aquifer, the concentration of contaminants in the water sampler can be related to the concentration of contaminants in the aquifer at the screened interval.

At each well to be sampled, an initial comparison should be done between the method of sampling according to the present invention and conventional sampling methods. The purpose of this comparison would be to account for potential borehole-specific interferences and to verify that data obtained using the present invention adequately represents data obtained using the standard sampling methodology.

It is thus seen that an improved method and apparatus for sampling groundwater can be utilized. It is also seen that the method and apparatus for water sampling according to this invention does not require purging of a well. It is also seen that the method and apparatus for water sampling according to this invention can be used subaqueously. It is also seen that the method and apparatus according to this invention precludes the need for using costly sorbents or dialysis cells. It is also seen that the method and apparatus according to this invention can utilize water as a carrier for volatile organic compounds and other contaminants. Furthermore, it is seen that the method and apparatus according to the present invention is economical, environmentally friendly, and easy to construct and use.

It is understood that many variations will become apparent to one of ordinary skill in he art upon reading the specification. Such variations are within the spirit and scope of the invention as defined by the following appended claims.

That which is claimed:

1. A passive water sampler for monitoring the concentration of contaminants in groundwater comprising:

a semipermeable membrane, said semipermeable membrane being permeable to said contaminants and impermeable to water;

said semipermeable membrane defining an inner chamber therein; and said inner chamber being at least partially filled with water, said partially filled semipermeable membrane being placed in contact with said groundwater thereby allowing said contaminants to diffuse through said semipermeable membrane and into said inner chamber, the concentrations of said contaminants in said groundwater and in said water coming into equilibrium.

2. The water sampler according to claim 1 wherein said water is distilled water.

3. The water sampler according to claim 1 further comprising a port communicating with said inner chamber, said port for adding or withdrawing water from said inner chamber.

4. The water sampler according to claim 3 wherein said port is connected to said semipermeable membrane by a washer.

5. The water sampler according to claim 3 wherein said port further comprises a locking nut.

6. The water sampler according to claim 3 wherein said port is made of polytetra fluoroethyline.

7. The water sampler according to claim 1 wherein said semipermeable membrane is made from polyethylene.

8. The water sampler according to claim 1 wherein said semipermeable membrane is provided in generally the shape of a tube having open ends, said open ends being sealed to form said inner chamber.

9. The water sampler according to claim 1 wherein said semipermeable membrane is provided as generally a flat piece, said flat semipermeable membrane being folded over and onto itself thereby creating a folded edge and three overlapping edges, said three overlapping edges being respectively sealed together to form said inner chamber.

10. The water sampler according to claim 1 further comprising two members attached to opposite sides of said semipermeable membrane, each said member having a grommet therein.

11. The water sampler according to claim 10 further comprising a weight hanging from one said grommet and a support line connected to the other said grommet, said weight to assist in submerging said water sampler in a well, said line for supporting said water sampler in said well and for raising said water sampler up and out of said well.

12. The water sampler according to claim 10 further comprising a weighted support line attached to at least one of said grommets, said weighted support line to assist in submerging said water sampler in a well, for supporting said water sampler in said well, and for raising and lowering said semipermeable membrane into and out of said well.

13. A method for determining the concentration of contaminants in groundwater comprising the steps of:

providing a semipermeable membrane, said semipermeable membrane being permeable to said contaminants and impermeable to water, manipulating said semipermeable membrane to define an inner chamber therein;

at least partially filling said inner chamber with said water;

placing said partially filled semipermeable membrane in contact with said groundwater, allowing said contaminants to diffuse through said semipermeable membrane and into said inner chamber;

allowing sufficient time for the concentrations of said contaminants in said groundwater and in said water to come into equilibrium;

withdrawing at least a portion of said water containing said contaminants from said inner chamber for analysis.

14. The method according to claim 13 further comprising the step of providing a port communicating with said inner chamber, and wherein said step of at least partially filling said inner chamber with water further comprises passing said water through said port and into said inner chamber, and wherein said step of withdrawing at least a portion of said water containing said contaminants from said inner chamber further comprises passing said contaminants out of said inner chamber through said port.

15. The method according to claim 13 wherein said step of at least partially filling said inner chamber with said water further comprises at least partially filling said inner chamber with distilled water.

16. The method according to claim 13 wherein said step of providing a semipermeable membrane further comprises providing a semipermeable membrane in the shape of a tube having open ends, and wherein said step of manipulating said semipermeable membrane to define an inner chamber therein further comprises sealing said open ends.

17. The method according to claim 13 wherein said step of providing a semipermeable membrane further comprises providing a semipermeable membrane as generally a flat piece, and wherein said step of manipulating said semipermeable membrane to define an inner chamber therein further comprises folding said flat semipermeable membrane over and onto itself, thereby forming a folded edge and three overlapping edges, said three overlapping edges being respectively sealed together.

18. The method according to claim 13 wherein said step of placing said partially filled semipermeable membrane in contact with said groundwater further comprises lowering said semipermeable membrane into a well, and wherein said step of removing said semipermeable membrane from contact with said groundwater further comprises raising said semipermeable membrane up and out of said well.

19. The method according to claim 18 further comprising the step of hanging a weight from said semipermeable membrane, said weight to assist in submerging said semipermeable membrane in said groundwater within said well.

20. The method according to claim 18 further comprising the step of attaching a weighted support line to said semipermeable membrane, said weighted support line to assist in submerging said semipermeable membrane in said groundwater within said well and for raising and lowering said semipermeable membrane into and out of said well.

\* \* \* \* \*

UNITED STATES PATENT AND TRADEMARK OFFICE
CERTIFICATE OF CORRECTION

PATENT NO. : 5,804,743

DATED : September 8, 1998

INVENTOR(S) : Don A. Vroblesky, William T. Hyde, Jr.

It is certified that error appears in the above-identified patent and that said Letters Patent is hereby corrected as shown below:

On the title page, item [73]:

and the United States of America, represented by the Secretary of the Interior.

Signed and Sealed this

Tenth Day of August, 1999

Attest:

Q. TODD DICKINSON

*Attesting Officer*     *Acting Commissioner of Patents and Trademarks*